(12) United States Patent
Ma

(10) Patent No.: US 10,340,985 B2
(45) Date of Patent: Jul. 2, 2019

(54) SYSTEM AND METHOD FOR TRANSFERRING POWER TO INTRABODY INSTRUMENTS

(71) Applicant: Covidien LP, Mansfield, MA (US)

(72) Inventor: Yong Ma, Shanghai (CN)

(73) Assignee: Covidien LP, Mansfield, MA (US)

( * ) Notice: Subject to any disclaimer, the term of this patent is extended or adjusted under 35 U.S.C. 154(b) by 81 days.

(21) Appl. No.: 15/594,855

(22) Filed: May 15, 2017

(65) Prior Publication Data

US 2017/0245950 A1 Aug. 31, 2017

Related U.S. Application Data

(63) Continuation of application No. 14/803,482, filed on Jul. 20, 2015, now Pat. No. 9,654,183, which is a
(Continued)

(51) Int. Cl.
*A61B 34/30* (2016.01)
*A61B 5/00* (2006.01)
(Continued)

(52) U.S. Cl.
CPC ......... *H04B 5/0037* (2013.01); *A61B 5/0002* (2013.01); *A61B 34/30* (2016.02);
(Continued)

(58) Field of Classification Search
CPC ......... A61B 19/00; A61B 34/30; A61B 34/35; A61B 34/37; A61B 34/20; A61B 34/25; A61B 34/70; A61B 5/00; A61B 5/05; A61B 5/0002; H02J 50/05; H02J 50/20

USPC ............. 307/104, 149, 66, 108; 607/60, 61; 600/424, 409, 407, 431, 437, 439; 606/133, 130
See application file for complete search history.

(56) References Cited

U.S. PATENT DOCUMENTS 5,423,334 A 6/1995 Jordan
5,704,352 A * 1/1998 Tremblay ............. A61B 5/0031
600/300
(Continued)

FOREIGN PATENT DOCUMENTS

WO 2009124174 A2 10/2009

OTHER PUBLICATIONS

Australian Patent Examination Report No. 1 dated May 23, 2013 for Australian Patent Appln. No. 2011200718.
(Continued)

*Primary Examiner* — Fritz M Fleming
*Assistant Examiner* — Jagdeep S Dhillon

(57) ABSTRACT

A system and method for transferring power includes a power transmitting unit for transmitting power and a power receiving unit for receiving power from the power transmitting unit. The power transmitting unit may be positioned outside a human body and the power receiving unit is located on an intrabody instrument adapted to be movable from the outside of the human body to inside the human body. The intrabody instrument may be a medical instrument connected to or incorporated within a robotic arm. The power transmitting unit may wirelessly transfer power to the power receiving unit in a continuous, non-interrupted manner.

18 Claims, 3 Drawing Sheets

Related U.S. Application Data continuation of application No. 13/024,503, filed on Feb. 10, 2011, now Pat. No. 9,107,684.

(60) Provisional application No. 61/310,786, filed on Mar. 5, 2010.

(51) Int. Cl.

| | | |
|---|---|---|
| *H04B 5/00* | (2006.01) | |
| *A61B 34/35* | (2016.01) | |
| *A61B 34/37* | (2016.01) | |
| *H02J 50/05* | (2016.01) | |
| *H04B 1/03* | (2006.01) | |
| *A61B 17/00* | (2006.01) | |

(52) U.S. Cl.
CPC ............ *A61B 34/35* (2016.02); *A61B 34/37* (2016.02); *H02J 50/05* (2016.02); *A61B 2017/00411* (2013.01); *A61B 2017/00734* (2013.01); *A61B 2034/301* (2016.02); *H04B 1/03* (2013.01)

(56) References Cited

U.S. PATENT DOCUMENTS

| | | | |
|---|---|---|---|
| 6,161,032 A * | 12/2000 | Acker | A61B 5/06 324/207.11 |
| 6,211,799 B1 * | 4/2001 | Post | A61B 5/0028 341/33 |
| 6,666,875 B1 | 12/2003 | Sakurai et al. | |
| 7,324,915 B2 | 1/2008 | Altmann et al. | |
| 7,379,775 B2 | 5/2008 | Parramon et al. | |
| 7,522,878 B2 | 4/2009 | Baarman | |
| 7,613,497 B2 | 11/2009 | Govari et al. | |
| 7,885,712 B2 | 2/2011 | Goetz et al. | |
| 8,239,001 B2 * | 8/2012 | Verard | A61B 5/062 600/407 |
| 9,107,684 B2 | 8/2015 | Ma | |
| 9,654,183 B2 | 5/2017 | Ma | |
| 2002/0107445 A1 * | 8/2002 | Govari | A61B 5/06 600/437 |
| 2002/0128644 A1 | 9/2002 | Hata et al. | |
| 2003/0074011 A1 * | 4/2003 | Gilboa | A61B 5/06 606/130 |
| 2005/0027192 A1 * | 2/2005 | Govari | A61B 5/06 600/424 |
| 2005/0123408 A1 * | 6/2005 | Koehl | F04D 15/0088 417/53 |
| 2005/0261552 A1 | 11/2005 | Mori et al. | |
| 2006/0004253 A1 | 1/2006 | Shigemori et al. | |
| 2006/0109125 A1 | 5/2006 | Overhultz et al. | |
| 2006/0149418 A1 | 7/2006 | Anvari | |
| 2006/0161223 A1 | 7/2006 | Vallapureddy et al. | |
| 2006/0253109 A1 | 11/2006 | Chu | |
| 2007/0021140 A1 | 1/2007 | Keyes et al. | |
| 2007/0137372 A1 | 6/2007 | Devengenzo et al. | |
| 2007/0238985 A1 * | 10/2007 | Smith | A61B 5/06 600/424 |
| 2007/0265690 A1 * | 11/2007 | Lichtenstein | A61B 5/06 607/116 |
| 2008/0111513 A1 | 5/2008 | Farritor et al. | |
| 2008/0147089 A1 * | 6/2008 | Loh | A61B 1/00149 606/130 |
| 2008/0221591 A1 | 9/2008 | Farritor et al. | |
| 2009/0039828 A1 | 2/2009 | Jakubowski | |
| 2009/0118610 A1 * | 5/2009 | Karmarkar | A61B 5/0476 600/420 |
| 2009/0145674 A1 * | 6/2009 | Lee | B60K 6/405 180/65.1 |
| 2010/0001687 A1 * | 1/2010 | Watanabe | B60L 3/12 320/109 |
| 2010/0030233 A1 | 2/2010 | Whitman et al. | |
| 2010/0185212 A1 | 7/2010 | Sholev | |
| 2010/0201202 A1 | 8/2010 | Kirby | |
| 2011/0015649 A1 | 1/2011 | Anvari et al. | |
| 2011/0077719 A1 | 3/2011 | Rofougaran et al. | |
| 2011/0115891 A1 | 5/2011 | Trusty | |
| 2011/0278948 A1 * | 11/2011 | Forsell | A61N 1/3787 307/104 |
| 2011/0301668 A1 * | 12/2011 | Forsell | A61N 1/37223 607/60 |
| 2012/0225619 A1 | 9/2012 | Charland | |
| 2013/0230005 A1 | 9/2013 | Dakshinamurthy et al. | |

OTHER PUBLICATIONS

Extended European Search Report corresponding to EP 11 25 0254.7, completed Feb. 13, 2015 and dated Feb. 24, 2015; (8 pp).

\* cited by examiner

SYSTEM AND METHOD FOR TRANSFERRING POWER TO INTRABODY INSTRUMENTS

CROSS REFERENCE TO RELATED APPLICATION

This application is a continuation of U.S. patent application Ser. No. 14/803,482, filed on Jul. 20, 2015, now U.S. Pat. No. 9,654,183, which is a continuation of U.S. patent application Ser. No. 13/024,503, filed on Feb. 10, 2011, now U.S. Pat. No. 9,107,684, which claims the benefit of and priority to U.S. Provisional Application No. 61/310,786, filed on Mar. 5, 2010, the entire contents of each of which are incorporated herein by reference.

BACKGROUND

Technical Field

The present disclosure relates to a surgical robotic instrument for performing surgery of the minimally invasive type on a human body to be operated upon and, more particularly, to a system and method for transferring power to the surgical robotic instrument.

Background of Related Art

Minimally invasive surgical procedures typically employ small incisions in body cavities for access of various surgical instruments, including forceps, laparoscopes, scalpels, scissors, and the like. It is often the case that several surgical hands, such as several laparoscopic instrument and camera holders, are necessary to hold these instruments for the operating surgeon during the particular surgical procedure. With the introduction of robotic-assisted minimally invasive surgery (MIS) in recent years, hospitals worldwide have made significant investments in acquiring this latest technology for their respective facilities.

Thus, it is known to use MIS when carrying out surgical operations. When surgery of this kind is performed, access to a subcutaneous surgical site is provided via a number (typically 3 to 5) of small (typically 5-12 mm) incisions, through which a surgical arm is manually passed. The surgical arms are then coupled to the surgical robotic instrument, which is capable of manipulating the surgical arms for performing the surgical operations, such as suturing or thermally cutting through tissue and cauterizing blood vessels that have been cut through. The surgical arms thus extend through the incisions during the surgery, one of which incisions is used for supplying a gas, in particular carbon dioxide, for insufflating the subcutaneous area and thus create free space at that location for manipulating the surgical instruments.

Open surgeries often require a surgeon to make sizable incisions to a patient's body in order to have adequate visual and physical access to the site requiring treatment. The application of laparoscopy for performing procedures is commonplace. Laparoscopic surgeries are performed using small incisions in the abdominal wall and inserting a small endoscope into the abdominal cavity and transmitting the images captured by the endoscope onto a visual display. The surgeon may thus see the abdominal cavity without making a sizable incision in the patient's body, reducing invasiveness and providing patients with the benefits of reduced trauma, shortened recovery times, and improved cosmetic results. In addition to the endoscope, laparoscopic surgeries are performed using long, rigid tools inserted through incisions in the abdominal wall.

However, conventional techniques and tools for performing laparoscopic procedures may limit the dexterity and vision of the surgeon. Given the size of the incisions, the maneuverability of the tools is limited and additional incisions may be required if an auxiliary view of the surgical site is needed. Thus, robotic instruments may be used to perform laparoscopic procedures. However, conventional robotic instruments are not continuously connected to external power sources for receiving a steady stream of power.

SUMMARY

In accordance with the present disclosure, a power transfer system is provided. The system includes a power transmitting unit for transmitting power and a power receiving unit for receiving power from the power transmitting unit. The power transmitting unit is positioned outside a human body and the power receiving unit is located on an intrabody instrument adapted to be movable from the outside of the human body to inside the human body.

In accordance with the present disclosure, a power transfer system is provided. The system includes a power transmitting unit for transmitting power and a power receiving unit for receiving power from the power transmitting unit. The power transmitting unit is positioned outside a human body and the power receiving unit is located on an intrabody instrument adapted to be movable from the outside of the human body to inside the human body.

In one embodiment, the power transmitting unit is connected to an energy source and the intrabody instrument includes at least an energy storage unit and one or more electronic components.

In yet another embodiment, the intrabody instrument is a medical instrument used in surgical procedures and in another embodiment the intrabody instrument is a robotic arm.

In still another embodiment, the power transmitting unit wirelessly transfers power to the power receiving unit in a continuous, non-interrupted manner. The power may be wirelessly transferred by using inductive coupling power transfer methodologies or the power may be wirelessly transferred by using radio frequency (RF) power transfer methodologies.

In another embodiment, if an energy source connected to the power transmitting unit is disconnected, the power receiving unit is automatically energized via an energy storage unit located within the intrabody instrument.

In yet another embodiment, the system further includes one or more data communications units for transferring data between the power transmitting unit and the power receiving unit. Additionally, the system further includes one or more data communications units for transferring data to one or more external sources or external control units.

A method for transferring power is also provided in accordance with the present disclosure. The method includes providing a power transfer system as described above. The method further includes transmitting power via a power transmitting unit and receiving power from the power transmitting unit via a power receiving unit. The power transmitting unit is positioned outside a human body and the power receiving unit is located on an intrabody instrument adapted to be movable from the outside of the human body to inside the human body.

In accordance with the present disclosure, a power transfer system is provided for wirelessly, continuously, and non-interruptedly transferring information. The system includes a transmitting unit connected to an energy source, the transmitting unit configured to transmit the information and a receiving unit including an energy storage unit and one or more electronic components, the receiving unit configured to receive the information from the transmitting unit. The transmitting unit is positioned outside a human body and the receiving unit is operatively associated with a robotic arm adapted to be movable from the outside of the human body to one or more positions inside the human body during surgical procedures.

BRIEF DESCRIPTION OF THE DRAWINGS

Various embodiments of the presently disclosed robotic instrument are described hereinbelow with references to the drawings, wherein.

DETAILED DESCRIPTION OF THE EMBODIMENTS

Figure 1:
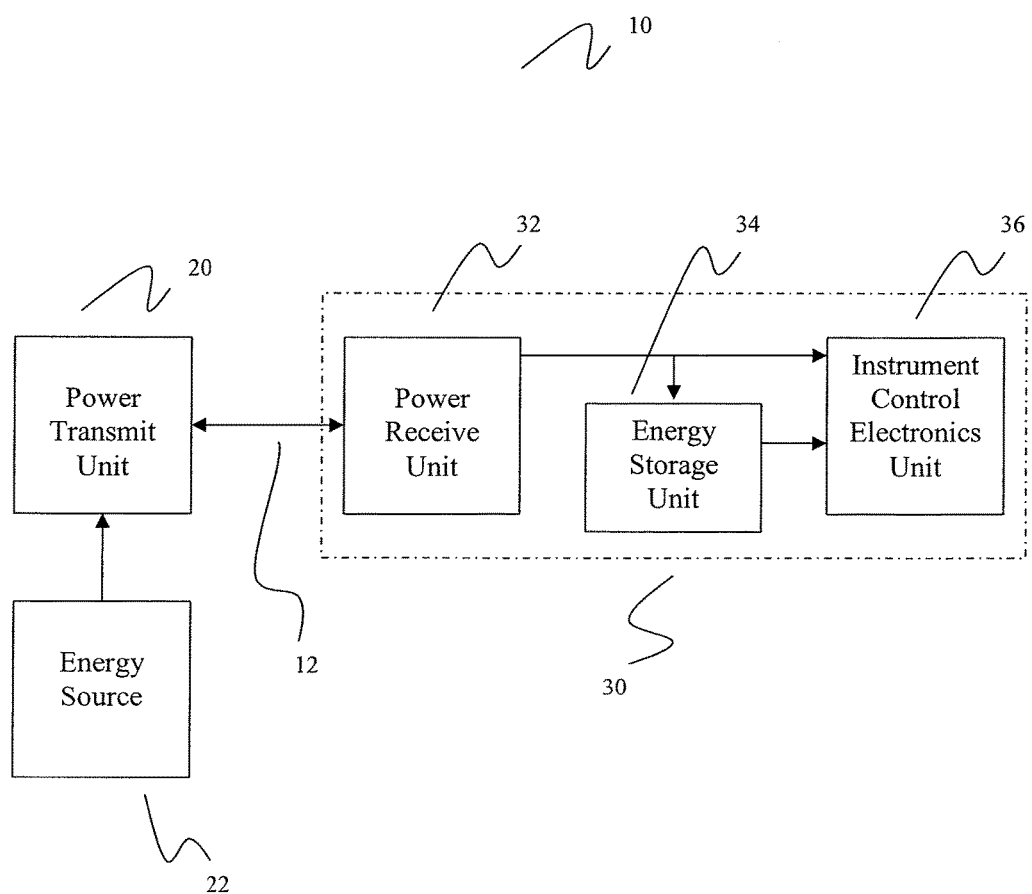
FIG. 1 is a block diagram of a power transfer system, in accordance with the present disclosure.

A more particular description of the present disclosure, briefly summarized above, may be had by reference to the embodiments of the present disclosure described in the present specification and illustrated in the appended drawings. It is to be noted, however, that the specification and appended drawings illustrate only certain embodiments of this present disclosure and are, therefore, not to be considered limiting of its scope. The present disclosure may admit to equally effective embodiments.

Reference will now be made in detail to exemplary embodiments of the present disclosure. While the present disclosure will be described in conjunction with these embodiments, it is to be understood that the described embodiments are not intended to limit the present disclosure solely and specifically to only those embodiments. On the contrary, the present disclosure is intended to cover alternatives, modifications, and equivalents that may be included within the spirit and scope of the present disclosure as defined by the attached claims.

It has been found that in some cases, if not in most cases, performing MIS procedures by means of a surgical robotic instrument has advantages in comparison with manually performed MIS. Such a surgical robotic instrument may comprise a so-called master, which may be controlled by a surgeon, and a so-called slave, being the surgical robotic instrument that performs the surgery in response to commands from the master, with a control system providing the required connection between the master and the slave. The slave robotic instrument may comprise surgical arms, each configured as a long narrow bar, at the distal end of which a small instrument may be provided, which instrument, just like the associated surgical arm, may be manipulated and controlled from the master. Such instruments may consist of, for example, thermal cutters, scissors, suturing tools, but also of an endoscope, by means of which the surgical site may be shown to the surgeon at the location of the master.

Furthermore, in robotically-assisted or telerobotic surgery, the surgeon typically operates a master controller to remotely control the motion of surgical instruments affixed to robotic arms positioned at the surgical site. The master controller may be in a location that may be remote from the patient (e.g., across the operating room, in a different room or a completely different building from the patient). The master controller usually includes one or more hand input devices, which are coupled to the robotic arms holding the surgical instruments, and the master controller controls servo motors associated with the robotic arms for articulating the instruments at the surgical site. During the operation, the hand devices provide mechanical articulation and control of a variety of surgical instruments, coupled to the robotic arms, that each perform various surgical functions for the surgeon. The exemplary embodiments of the present disclosure may refer to manually operated medical instruments or remotely operated medical instruments. The medical instruments may be a robotic arm or connected to a robotic arm. The medical instruments may be incorporated within the robotic aim or may be attached to the robotic arm. One skilled in the art may contemplate a plurality of different robotic systems and/or configurations, not limited to robotic arms for achieving the data/power transfer capabilities described herein.

With reference to FIG. 1, a block diagram of a power transfer system, in accordance with the present disclosure is presented. The system 10 includes a power transmit unit 20 in operable communication with a medical instrument 30 (or intrabody instrument). The medical instrument 30 may be a robotic arm. The power transmit unit 20 may be energized via an energy source 22. The robotic arm 30 may include a power receive unit 32, an energy storage unit 34, and an instrument control electronics unit 36. The power transmit unit 20 may communicate, preferably in a wireless manner, with the power receive unit 32 of the robotic arm 30 via a communication link 12.

The power transmit unit 20 may be used for transmitting power and the power receive unit 32 may be used for receiving power from the power transmit unit 20. The power transmit unit 20 may be positioned outside a human body and the power receive unit 32 may be located on an intrabody instrument (e.g., robotic arm 30) and may be adapted to be movable from the outside of the human body to inside the human body. The power transmit unit 20 may be connected to an energy source 22. The intrabody instrument 30 may include at least an energy storage unit 34 and an instrument control electronic unit 36. The energy storage unit 34 may be a battery. The instrument control electronics unit 36 may include logic controls and intrabody instrument drivers.

Additionally, it is contemplated that a plurality of robotic arms may be used, each one having power receiving means, energy storage means, and/or control logic means. The one or more robotic instruments may be positioned entirely within the body cavity of a human being or patient. However, it is contemplated that the one or more robotic instruments may be partially inserted through a cavity of patient. It is also contemplated that the one or more robotic aims communicate with each other by sharing information. Also, controllers included in the instrument control electronics unit 36 may be purchased off-the-shelf, constructed de novo, or off-the-shelf controllers may be customized to control the robotic components of the present disclosure. One skilled in the art would be able to select a controller appropriate for the robotic instrument or intrabody instrument or the microrobot.

In operation, the power transmit unit 20 preferably transmits power to the power receive unit 32 wirelessly. The power transmit unit 20 may wirelessly transfer power to the power receive unit 32 in a continuous, non-interrupted manner. The power may be wirelessly transferred by using inductive coupling power transfer methodologies, where the inductive coupling power transfer methodologies permit the power transmit unit 20 and the power receive unit 32 to share the same inductor-capacitor resonance frequency. Alternatively, the power may be wirelessly transferred by using radio frequency (RF) power transfer methodologies, where the RF power transfer methodologies permit the power transmit unit 20 and the power receive unit 32 to operate at a common frequency.

When selecting a power supply, an external power supply may be employed with a tethered configuration. However, exemplary embodiments embrace that the power be supplied by batteries. Versions of the robotic instrument or intrabody instrument of the present disclosure may use alkaline, lithium, nickel-cadmium, or any other type of battery known in the art. Alternatively, magnetic induction may be another possible source of power, as is piezoelectric induced energy. In addition, one of skill in the art may adapt other power sources such as nuclear, fluid dynamic, solar or the like to power the robotic instrument or intrabody instrument of the present disclosure.

Wireless power transmission or wireless energy transfer is generally the process that takes place in system 10 where electrical energy may be transmitted from a power source to an electrical load, without interconnecting wires. The system 10 also includes control logic that may be capable of transferring power that may be received by the wireless power-receiving device 32 to the wireless power-transmitting device 20. The control logic may be incorporated within the instrument control electronics unit 36. Accordingly, the power transfer system 10 disclosed herein may simultaneously receive and transmit power wirelessly.

For example, transmit circuitry (not shown) may produce an alternating voltage, having a predetermined frequency, from a direct current voltage supplied to the transmit circuitry during operation of the system 10 and supply the produced alternating voltage to a transmit coil. Also by way of example, the transmit circuitry may produce a predetermined level of intensity of an inductive field in a transmit coil. The control logic incorporated within the instrument control electronics unit 36 may comprise hardware alone (i.e., circuitry) or may include both hardware and software. The control logic incorporated within the instrument control electronics unit 36 may be implemented by one of ordinary skill in the electronic arts. This technology may include, for example, application specific integrated circuits, a microprocessor executing code that may be designed to implement the functions and methods described herein, programmable logic arrays, etc. The control logic incorporated within the instrument control electronics unit 36 may be capable of transferring power received by the wireless power-receiving device 32 to the wireless power-transmitting device 20. The control logic incorporated within the instrument control electronics unit 36 may transfer the power directly from the wireless power-receiving device 32 to the wireless power-transmitting device 20. For example, the control logic may supply the transmit circuitry with direct current voltage provided to the control logic from the receive circuitry.

In exemplary embodiments, a selectable power-transmitting protocol may include, for example, a particular frequency at which the transmit circuitry produces an alternating voltage that the transmit circuitry supplies to the transmit coil. Thus, selecting a first power-transmitting protocol may cause the transmit circuitry to produce an alternating voltage at a particular frequency and selecting a second power-transmitting protocol may cause the transmit circuitry to produce and alternating voltage at a different frequency. Analogously, a particular power-transmitting protocol may include, for example, a particular level of intensity of an inductive field for the transmitting coil. Thus, selecting a first power-transmitting protocol may cause the transmit circuitry to produce a particular level of intensity of the inductive field, whereas selecting a second power-transmitting protocol may cause the transmit circuitry to produce a different level of intensity for the inductive field.

Additionally, the system 10 may have a settings mechanism, providing a user of the system 10 with a means for selecting parameters for the operation of the system 10. The settings mechanism may comprise, for example, a plurality of selectable buttons with each selectable button having a power-transmitting protocol associated with it. Thus, the control logic incorporated within the instrument control electronics unit 36 may be capable of detecting when one of the selectable buttons may be selected. The control logic may also be capable of operating the wireless power-transmitting device 20 in accordance with the power-transmitting protocol associated with the selected buttons. In this manner, a user of the system 10 may choose a particular power-transmitting protocol that is best suited for a particular surgical procedure to be performed. For example, some surgical procedures may require more power to be consumed by the robotic instrument or intrabody instrument than other surgical procedures. As a result, a user of the system 10 may be able to control the amount of power transferred from the power transmit unit 20 to the power receive unit 32 by selecting a desired protocol.

Moreover, the power transmit unit 20 may be configured to transmit each of a plurality of different power levels via a respective one of a plurality of different frequency signals. For example, the power transmit unit 20 may transmit a low-power wireless transmission on a particular frequency to initially power up basic components of the system 10 for initial communications. The particular frequency at which the power transmit unit 20 transmits the low-level minimum power may be a fixed, pre-selected frequency signal that any of the robotic instruments may access. Additionally or alternatively, the transmitting unit may transmit power wirelessly using an automatic channel selection technique or an automatic channel switching technique that enables the receiving unit to automatically select a best channel (e.g., a frequency associated with the least amount of interference) prior to and during transmission. In other words, the user of the system 10 may enter a code relating a specific type of surgery and the system 10 may automatically determine the required power to be transmitted from the power transmit unit 20 to the power receive unit 32.

Furthermore, the stored information may also be used to implement a power conservation routine in which the robotic instruments are powered down or placed in a low-power mode when full operation of the robotic instruments may not be required. For example, the robotic instruments may enter into a low-power mode when only partial operation of the robotic instruments may be required. Alternately, if the energy source 22 connected to the power transmit unit 20 is disconnected, then the power receive unit 32 may be automatically energized via the energy storage unit 34 located within the intrabody instrument or robotic arm 30.

Moreover, in the illustrated examples described above, the layout of a process control system may not be limited by the locations of wired power sources or wired networks. Instead, field devices and other elements of a process control system may be located anywhere and use wireless power transmissions to receive power and wireless data communications to exchange data with other process control system devices or apparatus. Wireless power and data also enables reconfiguring the layout of process control systems relatively easier and quicker because relatively fewer cables or wires need to be moved or installed to relocate field devices.

In exemplary embodiments, the system 10 may also have a display mechanism (not shown) for providing a user with an indication of the operating status of the system 10. The display mechanism may include, for example, a power indicator (e.g., an LED) that indicates to a user that the system 10 is receiving power (see FIG. 2). The power indicator may light up, for example, when the wireless power-receiving device 32 of the system 10 is receiving power. Additionally, the power indicator may comprise a signal-strength meter, allowing the user to determine whether the signal transmitting the power is strong. The display mechanism may also include a battery-level indicator for the energy storage unit 34. The battery-level indicator may light up when the rechargeable battery (or energy storage unit 34) is fully charged. In other embodiments, a battery-level indicator may show approximately how much power is in the rechargeable battery (or energy storage unit 34). As a result, the user of the system 10 may be continuously informed or notified of the status of the power transferred from the power transfer unit 20 to the power receive unit 32.

Figure 2:
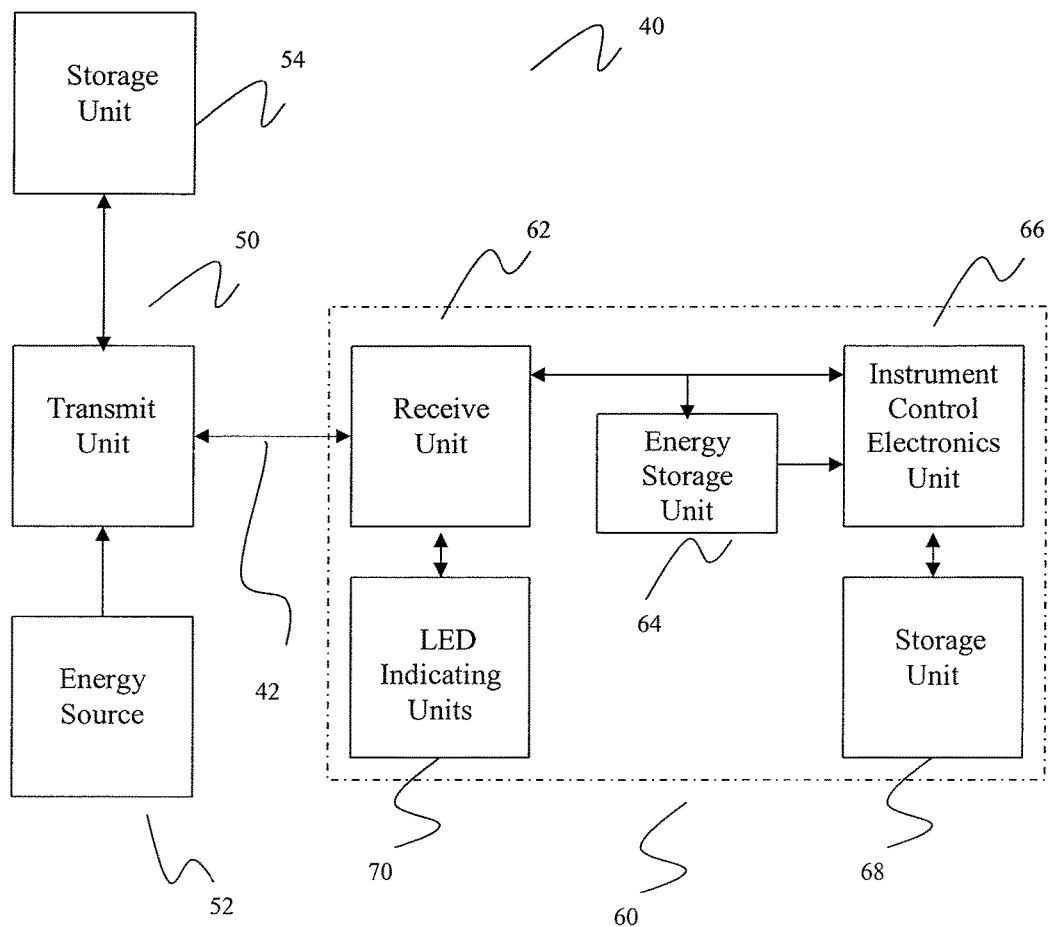
FIG. 2 is a block diagram of an information transfer system, in accordance with the present disclosure.

With reference to FIG. 2, a block diagram of an information transfer system, in accordance with the present disclosure is presented. The system 40 includes a transmit unit 50 and an intrabody instrument or robotic arm 60. The transmit unit 50 may be in operable communication with an energy source 52 and a storage unit 54. The robotic arm 60 may include a receive unit 62, an energy storage unit 64, an instrument control electronics unit 66, a storage unit 68, and an LED indicating unit 70. The transmit unit 50 may communicate with the receive unit 62 of the robotic arm 60 via a communications link 42.

Of course, several different types of connection components or communications links may be used to connect the transmit unit 50 to the receive unit 62. As used herein, "connection component" may be intended to refer to a wired or wireless connection between at least two components of systems 10, 40 that provide for the transmission and/or exchange of information and/or power between components. A connection component may operably couple consoles/displays (not shown) and robotic instruments to allow for communication between, for example, power components of robotic instruments and a visual display on, for example, a console.

According to one embodiment, connection components may be wired connections, such as a wire, cord, or other physical flexible coupling. The wired connections may be coupled at one end to robotic instrument and at a second end to, for example, a console/display. For purposes of this application, the physical or wired connection may also be referred to as "tethered" or "a tether." The wired connection may be any physical component that may be flexible, pliable, or otherwise capable of being easily formed or manipulated into different shapes or configurations.

The wireless connection may be referred to herein as "untethered." An "untethered device," "wireless device," or "wireless connection" may be intended for purposes of this application to mean any robotic instrument that may be fully enclosed within the patient's body such that no portion of robotic instrument may be external to the patient's body for at least a portion of the surgical procedure or, alternatively, any robotic instrument that operates within the patient's body, even partially, while not being physically connected to any external object for at least a portion of the surgical procedure.

The storage units 54, 68 may include any desired type of volatile and/or non-volatile memory such as, for example, static random access memory (SRAM), dynamic random access memory (DRAM), flash memory, read-only memory (ROM), etc. The storage units 54, 68 may include any desired type of mass storage device including hard disk drives, optical drives, tape storage devices, etc. The storage units 54, 68 may store information related to a plurality of different components within the transmit unit 50 and the robotic arm 60. The information stored in the storage units 54, 68 is further described below.

The LED indicating units 70 may inform or notify or indicate to the user of systems 10, 40 whether power is transferred between the transmit unit 50 and the receive unit 62.

Figure 3:
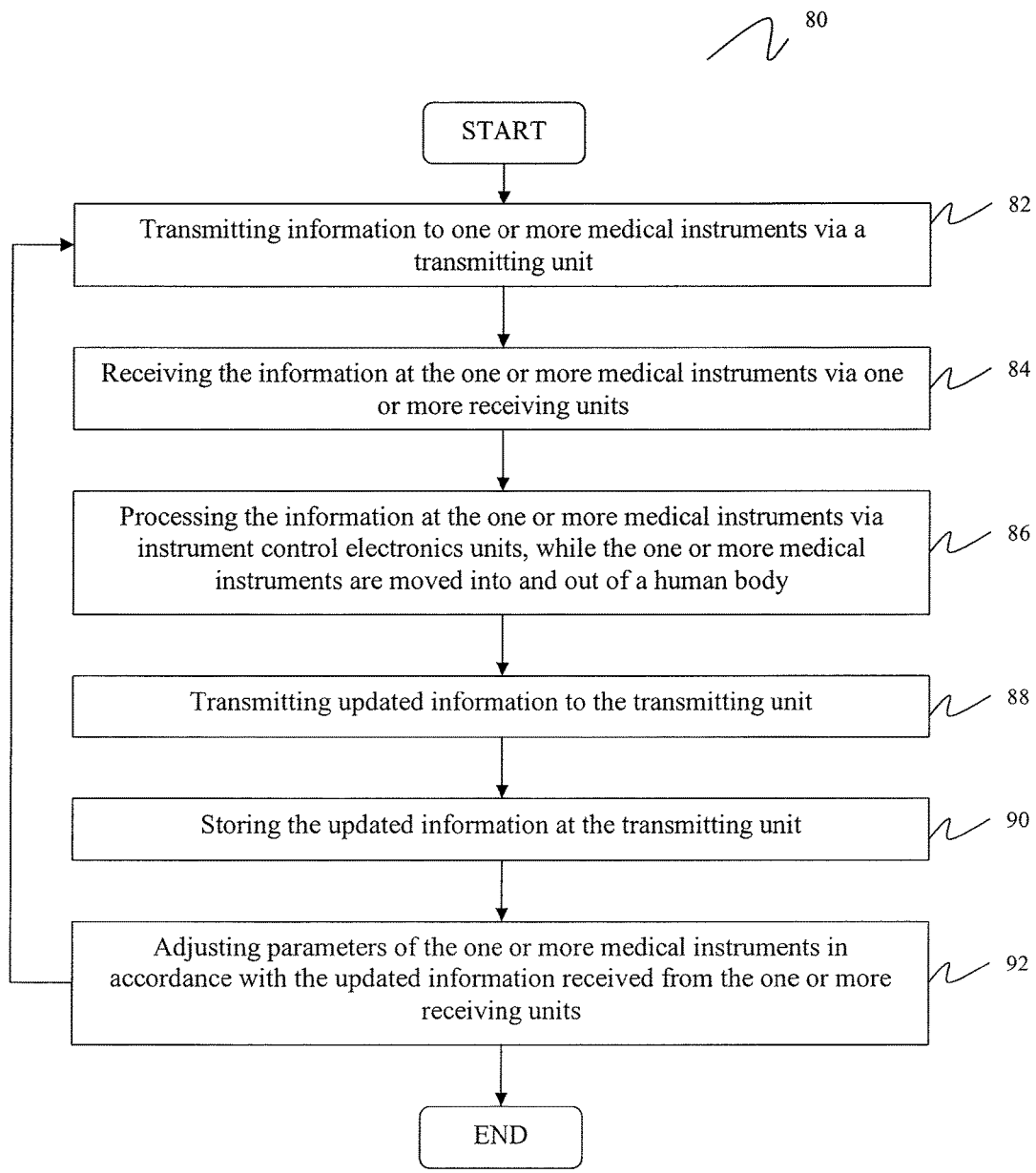
FIG. 3 is a flowchart illustrating power transfer between a transmitting unit and a receiving unit, in accordance with the present disclosure.

With reference to FIG. 3, a flowchart 80 illustrating power transfer between a transmitting unit and a receiving unit, in accordance with the present disclosure is presented.

In step 82, information (data/power) may be transmitted to the one or more medical instruments via a transmitting unit. In step 84, the information may be received by the one or more medical instruments via the one or more receiving units. In step 86, the information may be processed at the one or more medical instruments via the instruments control electronics unit, while the one or more medical instruments are moved into and out of a human body. In step 88, the updated information may be transmitted to the transmitting unit. In step 90, the updated information may be stored in a storage unit in operable communication with the transmitting unit. In step 92, one or more parameters of the one or more medical instruments may be adjusted in accordance with the updated information received from the one or more receiving units. The process then ends for the first cycle or first iteration. However, the process may be a continuous iterative process. In other words, the steps of the process may repeat for a number cycles or iterations, where parameters of the medical instruments are constantly adjusted.

In an alterative embodiment, an operating room table would contain electrical and mechanical interfaces for several surgical robotic manipulators or arms or instruments. The robotic instruments may be remotely controlled by using a plurality of consoles or external sources (e.g., surgical workstations, personal computers, etc.) preferably located away from the operating room table, such as but not limited to within a hospital as connected to a hospital local network and/or a remote network, such as the Internet. The control consoles may operate in conjunction with the one or more robotic instruments that may be positioned in a body cavity of a human being or patient. That is, the control consoles may be used to operate the one or more robotic instruments inside the body cavity of the patient. As used herein, "console" may be intended to refer to a controller or operational hub. A plurality of visual displays may be connected to the plurality of consoles for providing visual feedback of the body cavity as captured by the one or more robotic instruments.

In one embodiment, the visual display may be a standard video monitor. In an alternative embodiment, the visual display may display two dimensional visual feedback, three dimensional visual feedback or stereoscopic imaging to a surgeon via an imaging component on the one or more robotic instruments. Those of ordinary skill in the art will recognize that a signal from a camera may be processed to produce a display signal for many different types of display devices, including, but not limited to: televisions configured to display an NTSC (national television system committee) signal, televisions configured to display a PAL (phase alternating line) signal, cathode ray tube based computer monitors, LCD (liquid crystal display) monitors, and plasma displays.

The robotic instruments may be connected to base stations (not shown) that are connected to the operating room tables. The base stations may include a data signal connector for receiving/transmitting data to and from the robotic instruments (e.g., camera signals, position sensor signals, power signals, etc.), a control signal connector for transmitting control signals (and receiving feedback signals) to actuated components of the robotic instruments (e.g., motors, camera operation, etc.), and a power supply connector for supplying the requisite electrical and/or mechanical (e.g., pneumatic, hydraulic) power to actuated components of the robotic instruments. It is recognized that data, control signal, and power requirements for robotic instruments may vary depending upon the specific designed surgical task of the robotic instruments (e.g., high voltage vs. low voltage, number of actuators, tool operational requirements, etc.). Further, it is recognized that the physical dimensions, strength, weight, and stiffness of the base stations, and the connection therebetween are designed to provide a stable base for operation of the attached robotic instruments. Of course, the robotic instruments may not be connected to base stations connected to an operating table. The robotic instruments may be manually operated by, for example, a surgeon.

In an alternative embodiment, the robotic instruments may be in communication with a communication manager of the consoles via communication capabilities of the base stations. The base stations may be linked through a wire based connection to a wired communication link of the console. It is recognized that the connection and the link may be in an existing operating room communication infrastructure network, such that the base stations may be attached to an electrical/mechanical connection harness. It is recognized that the connection and link may be fully compatible with IP fiber optic network protocols for connection to the remote consoles for control of the robotic instruments via the base stations. Each of the base stations and/or robotic instruments may have assigned IP addresses to facilitate communication with the console via the communication manager. For example, IP addresses may be assigned to arm controllers in the controller unit. The network may also include switches and routers as is known in the art to enable communication with other telecommunication devices connected to the room network. Examples of the network protocols may be such as but not limited to Ethernet/IP and TCP/IP. However, as will be readily appreciated by those having ordinary skill in the art, any other suitable communication medium and protocol could be used.

In yet another alternative embodiment, a computer may have software for operating the robotic instruments. The computer may include a network connection interface, such as a wireless transceiver or a wired network interface card or a modem, coupled via connection to a device infrastructure. The connection interface may be connectable during operation of the console to the network. The network may support the transmission of data/signaling in network messages between consoles and the robotic system. The consoles may also have a user interface (including hand controllers), coupled to the device infrastructure by connection, to interact with a user (e.g., surgeon). The user interface may include one or more user input devices such as but not limited to a keyboard, a keypad, a track wheel, a stylus, a mouse, a microphone and the user output device such as a display screen and/or a speaker. If the screen is touch sensitive, then the display may also be used as the user input device as controlled by the device infrastructure. The user interface may be employed by the user of the console to coordinate messages or instructions over the network for operation of the robotic instruments.

Operation of the console may be enabled by the device infrastructure. The device infrastructure may include a computer processor and a memory module/unit. The computer processor may manipulate the operation of the network interface and the user interface by executing related instructions, which are provided by an operating system and the software. Further, it is recognized that the device infrastructure may include a computer readable storage medium coupled to the processor for providing instructions to the processor and/or to load/update the software in the memory module. The computer readable medium may include hardware and/or software such as, by way of example only, magnetic disks, magnetic tape, optically readable medium such as CD/DVD ROMS, and memory cards. In each case, the computer readable medium may take the form of a small disk, floppy diskette, cassette, hard disk drive, solid state memory card, or RAM provided in the memory module. It should be noted that the above listed example computer readable mediums may be used either alone or in combination.

In yet another alternative embodiment, a number of information managers may be used to control and manipulate the information. A communication manager may provide for communication of data signals to/from the data manager and communication of control signals to/from the control manager. A database manager may provide for such as but not limited to access of image data to/from an image database, data related to the functioning/set-up of various elements of the robotic instruments, and various position/orientation sensor data, and for providing data as needed to the position and orientation manager. A control manager may provide for monitoring the operation of the robotic instruments. A position/orientation manager may be responsible for such as but not limited to receiving sensor data from the data manager for calculating the position and orientation of the robotic instruments. A calculated position/orientation information manager may be made available to such as but not limited to the actuation of the display manager and the control manager. A configuration manager may provide for such as but not limited to dynamic configuration of the robotic instruments for a particular surgical procedure. The dynamic configuration may be automatic, semi-automatic, and/or manual operator intervention. A display manager of the software may coordinate/render the calculated position/orientation information and the patient/tool images on a display of a console of the user interface, as directed by the operator, for example, a surgeon.

In one implementation, by positioning robotic instrument within a body cavity relative to console, the power transfer system 10 may allow the surgeon to determine and maintain spatial orientation of robotic instrument with respect to the one or more consoles. Other benefits of system 10 may include, but are not limited to: providing a training tool for surgeons, reducing or eliminating the need for a surgeon to be on-site, and reducing the cost of robotic surgical systems.

In yet another exemplary embodiment, two or more robotic instruments may be operably coupled to each other as well as to an external unit (e.g., a console, or personal computer or network, etc.). According to one embodiment in which there are two robotic instruments, the two robotic instruments may be operably coupled to each other and an external unit by a flexible wired connection or a wireless connection. That is, the two robotic instruments may be operably coupled to each other by a flexible wired connection that may be coupled to each robotic instrument and each robotic instrument may also be operably coupled to an external unit by a flexible wired connection.

In summary, the present disclosure facilitates the application of laparoscopy and other minimally invasive surgical techniques to a much wider range of procedures by providing semi-autonomous and autonomous manually or remotely controlled robotic instruments that are used inside the body, especially human bodies. The present disclosure provides robotic in vivo wired and wireless manipulator, imaging, power, and sensor devices that may be inserted in the area to be treated, for example, the abdomen. The devices overcome the limitations associated with current generation laparoscopic cameras and tools, providing the surgical team a view of the surgical field from multiple angles, in vivo patient monitoring capability, and in vivo manipulator dexterity, as well as power control capabilities. It is contemplated that the instant in vivo robot could help the surgeon directly manipulate tissue. It is also contemplated to continuously and non-interruptedly provide power capabilities to the robotic devices. In other words, it is contemplated to continuously and wirelessly transfer power from the outside of the patient to any robotic intrabody instrument. Thus, unlike known systems that require field device power (e.g., alternating current (AC) power or direct current (DC) power) to be provided via electrical wires or cables and/or via a battery, the example systems and methods described herein may be used to implement field devices (e.g., a temperature sensor, a pressure sensor, a status (open/closed) sensor, an actuator, a power sensor, etc.) in a process control system that operate using wirelessly transmitted power and that communicate wirelessly within the process control system. From the foregoing and with reference to the various figure drawings, those skilled in the art will appreciate that certain modifications may also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for transferring power, the method comprising:
transmitting power via a power transmitting unit positioned outside a patient body;
receiving power from the power transmitting unit via a power receiving unit located on an intrabody instrument that is adapted to be at least partially inserted into the patient body and movable therein; and
wirelessly coupling the intrabody instrument to a second intrabody instrument that is positionable within the patient body such that the intrabody instrument and the second intrabody instrument electrically communicate with one another.

2. The method according to claim 1, further comprising receiving power at the power transmitting unit from an energy source coupled to the power transmitting unit.

3. The method according to claim 2, further comprising storing energy in an energy storage unit disposed within the intrabody instrument.

4. The method according to claim 3, further comprising energizing the power receiving unit from the energy storage unit in response to the power transmitting unit being disconnected.

5. The method according to claim 1, further comprising storing energy in a battery disposed within the intrabody instrument.

6. The method according to claim 1, wherein the power transmitting unit wirelessly transfers power to the power receiving unit.

7. The method according to claim 6, wherein the power transmitting unit wirelessly transfers power to the power receiving unit in a continuous, non-interrupted manner.

8. The method according to claim 6, wherein the power transmitting unit wirelessly transfers power using inductive coupling power transfer.

9. The method according to claim 8, wherein the power transmitting unit wirelessly transfers power using inductive coupling power transfer at a common inductor-capacitor resonance frequency.

10. The method according to claim 6, wherein the power transmitting unit wirelessly transfers power to the power receiving unit using radio frequency (RF) power transfer.

11. The method according to claim 10, wherein the power transmitting unit wirelessly transfers power to the power receiving unit using radio frequency (RF) power transfer at a common frequency.

12. The method according to claim 6, wherein the power transmitting unit wirelessly transfers power to the power receiving unit through control electronics disposed within the intrabody instrument.

13. The method according to claim 1, further comprising transferring power from the power receiving unit to the power transmitting unit.

14. The method according to claim 13, wherein the power receiving unit wirelessly transfers power to the power transmitting unit.

15. The method according to claim 1, further comprising receiving an input from a user, the input being a selection of a desired power-transmitting protocol.

16. The method according to claim 1, further comprising displaying, via a display mechanism, an operating status of the transmitting unit or the receiving unit.

17. The method according to claim 1, further comprising transferring data between the power transmitting unit and the power receiving unit via a data communications unit.

18. The method according to claim 1, further comprising assembling the intrabody instrument inside the patient body.

* * * * *